United States Patent [19]

Deane

[11] 4,025,201

[45] May 24, 1977

[54] METHOD AND APPARATUS FOR VIDEO INSPECTION OF ARTICLES OF MANUFACTURE BY DECUSSATE PATHS OF LIGHT

[75] Inventor: David W. Deane, Muncie, Ind.

[73] Assignee: Ball Brothers Service Corporation, Muncie, Ind.

[22] Filed: Apr. 21, 1975

[21] Appl. No.: 570,105

[52] U.S. Cl. .................. 356/240; 209/111.7 T; 250/223 B; 358/106
[51] Int. Cl.² ..................................... G01N 21/32
[58] Field of Search ............ 356/163, 239, 240; 250/223 B; 350/177, 174; 178/DIG. 36, DIG. 37; 209/111.7

[56] References Cited

UNITED STATES PATENTS

| 2,660,087 | 11/1953 | Domeshek | 350/174 |
| 2,798,605 | 7/1957 | Richards | 356/240 |
| 3,549,890 | 12/1970 | Keller | 250/223 B |
| 3,684,385 | 8/1972 | Einfalt et al. | 356/240 |
| 3,746,784 | 7/1973 | Van Oosterhout | 250/223 B |
| 3,858,983 | 1/1975 | Foster et al. | 356/163 |
| 3,932,042 | 1/1976 | Faani et al. | 356/240 |

Primary Examiner—Vincent P. McGraw
Attorney, Agent, or Firm—James D. Haynes

[57] ABSTRACT

Method and apparatus for detecting defects in articles of manufacture wherein the article is inspected in at least two different planes. Decussate light paths are directed through the article and the light transmitted by the article is directed to a video camera to produce dual images which are scanned to sense defects in the article and produce a reject signal when a defect is present.

10 Claims, 3 Drawing Figures

METHOD AND APPARATUS FOR VIDEO INSPECTION OF ARTICLES OF MANUFACTURE BY DECUSSATE PATHS OF LIGHT

BACKGROUND OF THE INVENTION

This invention relates broadly to an assembly for detecting defects in articles of manufacture and more specifically relates to the apparatus for automatically detecting defects in glassware.

It is oftentimes necessary to monitor articles of manufacture to assure that desired product quality levels are achieved. It is readily apparent, for example, to those having knowledge in the manufacture of glassware that finished glassware products may not be perfectly formed and may therefore in some cases not be entirely suitable for the use intended. By providing monitoring or inspection devices to eliminate those articles of manufacture which are not entirely suitable and therefore considered defective for a specific use, product quality can be enhanced. In glassware "spikes" which are sharp glass projections formed in glassware and "birdswings" which are found generally in bottles and which comprise thin pieces of glass extending across opposite inner walls thereof are examples of items for which glassware is often inspected and glassware rejected if present. Obviously, monitoring or inspection systems and a degree of reliability inherent in any such system for monitoring unwanted characteristics in finished glassware products or other such articles of manufacture are often important in achieving quality of the product.

Heretofore monitoring systems for detecting defects in glassware have taken various forms ranging from, for example, mere visual inspection utilized in the slow production of glassware to complex electronic detection systems utilized in the more rapid production of glassware. One such inspection apparatus is disclosed in application for patents Ser. No. 520,227, filed Nov. 1, 1974, and entitled "Method and Apparatus for Video Insepection of Articles of Manufacture." In that application a light source is positioned adjacent one side of and optically spaced from an article to be inspected. A video camera is positioned on the opposite side of the article from the diffused light source and scans the illuminated article in order to produce a video signal indicative of the difference in the refraction characteristics of the article to thereby indicate the presence or absence of defects in the glassware sample. Circuitry is disclosed for discriminating between true defects and lettering, mold marks, and coloring normally associated with the article. In the event there is a defect, an electrical processing circuit connected to the video camera and responsive to the video signal is provided for actuating a glassware rejection mechanism. Circuit means are also disclosed for inspecting round objects, such as the bottoms of round jars or glasses.

As an example of an early electronic inspection device, Fedorchak disclosed in U.S. Pat. No. 2,649,500 a glass inspective apparatus wherein ultraviolet light was directed into the inside of a bottle. The ultraviolet light was reflected out of the bottle onto a mosaic which was in turn scanned by a cathode-ray tube. The cathode-ray tube scanned the mosaic in a spiral manner to thereby provide indication when a flaw, such as a sharp projection, occurred in the bottle. This apparatus had the drawback in that a lamp had to be positioned such that light could be directed into the inside of the bottle so that the light would be reflected therefrom. This prohibited rapid assembly line inspecting of bottles. In addition, no means were taken into account for the change in reflected ultraviolet light due to the corners of the glass jar and for other normal variances in the contour of the bottle caused by, for example, seams and lettering.

A more recent development was disclosed by Gambrell et al in the U.S. Pat. No. 3,379,829 wherein a fault detection apparatus wwas disclosed wherein normal pertubations in the glassware were not detected because a mask corresponding to the shape of the inspected article of manufacture provided blanking signals when normally encountered pertubations on the surface were scanned by an electronic beam. Such an arrangement, however, requires that the mask be appropriately aligned with the article being inspected and eliminates the possibility of checking flaws positioned between the masked portion of the article and the source of radiation which is detected.

Richards disclosed in U.S. Pat. No. 2,798,605 an electronic inspection apparatus for detecting foreign matter in bottles. In the Richards' invention, bottles are passed along a conveyor line and are passed in front of the optical system of a television camera. As each object passes in front of the camera, a light flash of short duration is provided to thereby illuminate the object and cause an image to be transmitted to the mosaic of the television camera tube. The mosaic is scanned by the cathode-ray gun of the camera tube which provides an output signal that indicates appreciable discontinuity in the video signal from its average level. However, this invention requires a rather complex "herringbone" sweep action in order for the inspection apparatus to distinguish between the sides of the bottle and true defects. Further, two transverse views are required of each bottle in order to detect flaws along the vertical length of the bottle, thereby requiring two separate camera systems, thus, while Richards was an improvement in the art, the method and apparatus required for inspecting the bottles remained quite complex.

While the above-referenced patents disclose various methods and apparatus for detecting imperfections in glassware, if the defect were in a position near the edge or outside portion of the container as viewed by the television camera, the defect would not be detected. While some systems are available wherein the bottle is rotated during the inspection cycle, no system is known to the applicant hereof wherein the glassware is inspected in such a manner that any defect within the area of inspection is certain to be determined.

Accordingly, it is an object of the present invention to provide a new and improved method and apparatus for monitoring and detecting defects in articles of manufacture such as glassware which is more dependable and accurate than those found in the prior art.

Another object of the present invention is to provide a new and improved apparatus for electronically monitoring detecting defects in glassware without stopping the glassware during the inspection cycle and without rotating the glassware during the inspection cycle.

SUMMARY OF THE INVENTION

Accordingly, this invention relates to a method and apparatus for detecting defects in articles of manufacture, such as glassware, wherein the glassware is inspected in at least two different planes. Light is directed through the article by at least two different light sources and the dual images thus produced are viewed by a single camera. In this manner, defects that are in regions of nondetectability when viewed with a single lamp source are detected by the alternate lamp source. The present invention resides in the particular configuration and arrangement of the lamps, the article being inspected, the mirrors and the viewing camera whereby decussate paths of light impinge on the article being inspected to alternately provide dual images to the camera. As the light paths impinge on the camera they are juxtaposed such that the resulting images viewed by the camera and the detecting apparatus are scanned or sensed for defects during one integration period of the viewing device.

BRIEF DESCRIPTION OF THE DRAWINGS

Other objects, features and advantages of the present invention will become more fully apparent from the appended claims and the accompanying drawings in which:

DETAILED DESCRIPTION OF THE PREFERRED EMBODIMENT

Figure 1:
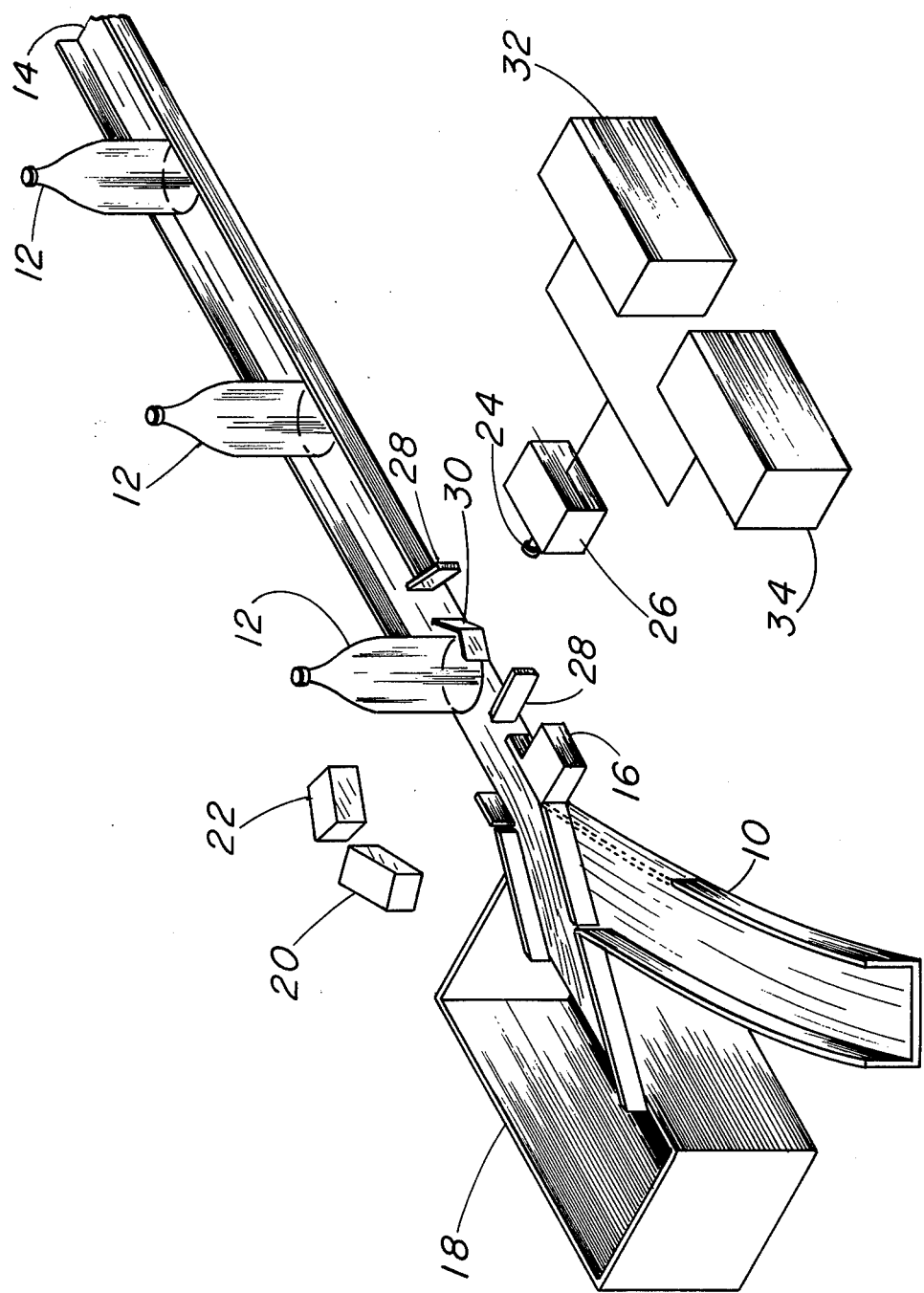
FIG. 1 is a partial prospective view and partial block diagram of an electronic video defect detection assembly constructed in accordance with the preferred embodiment of the present invention and preferrably provided for detecting defects in a train of glass bottles transported along a conveyor mechanism.

Turning now to the drawings wherein like components are designated by like reference numerals throughout the various figures, the electronic inspection system of the present invention is disclosed. Referring to FIG. 1 there is illustrated a conveyor mechanism 10 positioned between various components of the electronic video inspection apparatus of the present invention for transporting a train of glassware, such as for example, glass bottles 12 past the assembly in the direction indicated by arrow 14. The glassware may be in the form of round bottles or flask and the bottles may be in any desired shading or coloration.

As each bottle passes the inspection assembly it is inspected for defects or abnormalities generally such as, for example, spikes or birdswings. In the event a defective bottle is detected, the electronic video assembly actuates a gate 16 positioned downstream of the assembly for directing the defective bottle away from the conveyor mechanism and into a reject platform or container 18. In this manner only the acceptable bottles are allowed to reach their ultimate destination on the conveyor mechanism for further processing. While a reject gate and platform or container are illustrated, it should be understood that any suitable reject means for removing a defective bottle from the conveyor may be provided. Thus, for example, a push-out arm (not shown) may be utilized for pushing the defective bottle off the conveyor mechanism.

As illustrated in the figure, the electronic video assembly includes a light source 20 and a light source 22 positioned on one side of and in close proximity to the conveyor mechanism 10 for illuminating each of the glass bottles 12 as the bottles pass thereby. Light sources 20 and 22 are semi-diffused light sources designed to illuminate the object under inspection with a limited bundle of light rays. That is, the rays act neither as though they originated at a point source, as in a shadow-graph, nor from a truly diffuse illuminate. The solid angular extent of the illuminating ray bundle at any point in the object plane determines the sensitivity of the optical image to changes in the refraction of the object under inspection. The smaller the ray bundle, the less the refraction change in the object under inspection needed to move the majority of the bundle out of the acceptance aperture of the camera imaging lens 24. The converse is true when the ray bundle subtends a larger solid angle. The greater the portion of the bundle through any point which escapes the acceptance aperture of the camera lens, the darker that point appears in the image. In the preferred embodiment of this invention the extent of the ray bundle through each point is designed to more than fill the acceptance aperture of the imaging lens.

The limited ray bundle passing through each point can be obtained from a diffuse source at a considerable distance from the object, or an optical system imaging an extensive source upon the camera lens, or other optical means. It should be noted that a more uniform distribution of light rays may be obtained if the semi-diffused light sources are positioned farther away from the object under inspection. This, however, is not practical when the electronic video assembly is utilized in the typical glass manufacturing plant where space is at a premium. Accordingly, to solve this problem, an optical distance producing lens may be mounted within the light sources or at some point between the light source and the conveyor mechanism 10. The optical distance producing lens which may be of any conventional design directs the light rays emanating from the sources 20 and 22 onto and through the passing bottles 12 as if the light sources were substantially farther away from the conveyor mechanism thereby to provide for a more uniform light distribution through the bottles 12.

A video camera 26 which is positioned on the side of the conveyor mechanism 10 opposite the light sources 20 and 22 and in alignment with reflecting means 28 and 30 is provided for scanning each of the passing illuminated bottles so as to produce a representative standard video signal which, if desired, may be applied to a standard video monitor or display tube 32. At this point it should be noted that sudden changes in the refraction characteristics of the glass bottle being examined causes the light passing through these regions to be deflected in radically different directions compared to the direction of refraction of the light by the surrounding material forming the glassware. As a result in those regions where the glass has pertubations such as flaws, changes in thickness, lettering, etc., light passing therethrough appears darker than those regions displaying uniform thickness as do darker defects and occlusions. Accordingly, the image of the detected bottle on a screen of display tube 32 would include dark areas representing defects within the bottle.

It should be understood that the video display tube is not required for the proper operation of the electronic bottle inspection apparatus of the present invention. However, it may be of significant aid in initially calibrating the system and would be of assistance in understanding the operation of the system.

The video signals produced by camera 26 are also directed to electronic circuits 34 for processing the video signals. The circuits act upon the video signal to isolate signals representative of defects in the glassware being inspected. Since camera imaging lens 24 is receiving a path of light from each light source, the video display tube will actually display two images of the bottle presently under inspection. When a defect signal is detected in either image or view of the bottle, the processing circuit 34 generates a reject signal which is applied to the reject gate 16 for actuating the reject gate and deflecting the defected bottle onto the reject platform 18.

U.S. Pat. No. 3,746,784 of VanOosterhout and pending U.S. application Ser. No. 520,227, filed Nov. 1, 1974, of VanOosterhout, both being assigned to the common assignee herewith, disclose circuitry for evaluating the video signals and producing defect detection signals.

Figure 2:
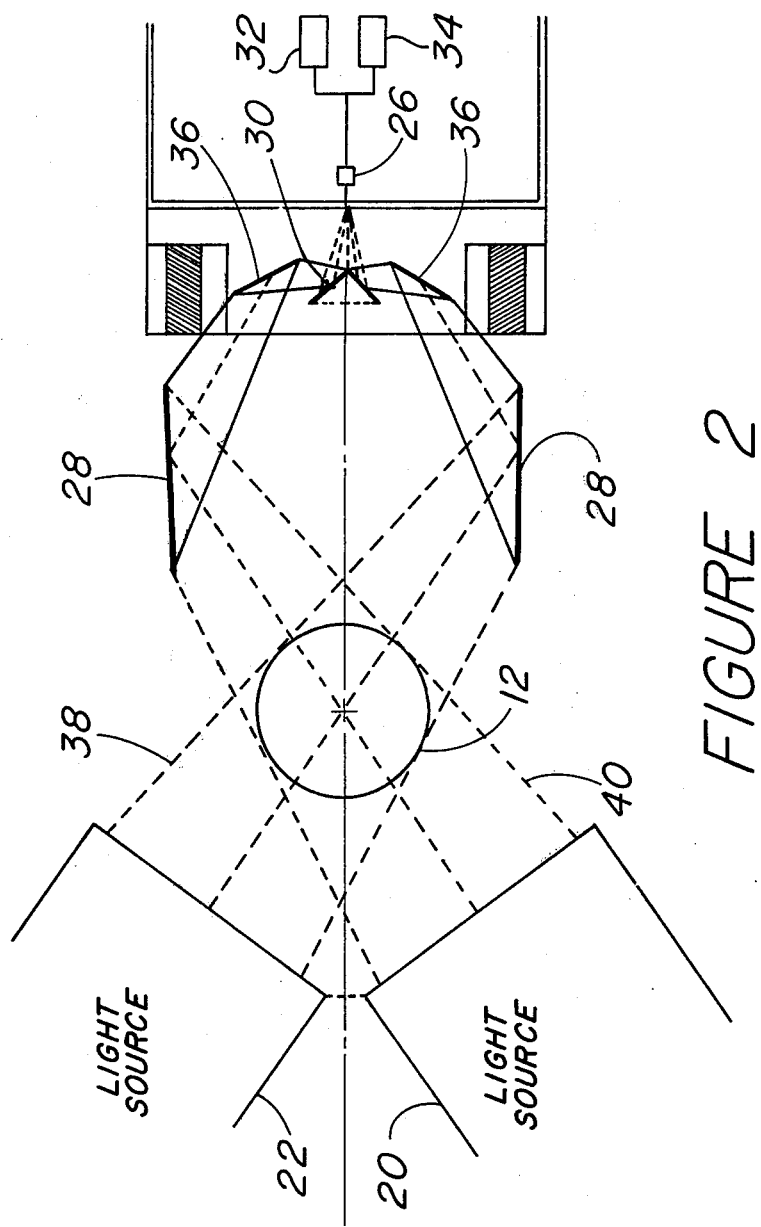
FIG. 2 is a schematic diagram of the preferred embodiment of the video inspection apparatus of the present invention.

Referring to FIG. 2, the various components of the present invention are shown as viewed from the top. The embodiment presented in FIG. 1 utilized only a first reflecting means 28 and a second reflecting means 30. FIG. 2 discloses an additional reflecting means 36. The various paths of light are shown in a single line representation. Both paths of light 38 and 40 are viewed simultaneously by camera 26. Reflecting means 28, 30 and 36 are located to bring these paths of light into juxtaposition at the camera imaging lens of video camera 26. Accordingly, camera 26 views an image engendered by light path 38 and an image engendered by light path 40, simultaneously. Both images are scanned for defects with the result that all areas of the article or glass container under inspection are viewed and inspected during a single integration period or inspection period of the inspecting apparatus. The light paths 38 and 40 are shown in single line representation by dotted lines located in the center of the light paths. While light paths 38 and 40 are shown to be totally reflected by reflecting means 30, this is not an absolute necessity. However, by accurately placing reflecting means 28, 36 and 30, all of the light may be reflected and viewed by video camera 26. By having the light paths emerge from reflecting means 30 juxtaposed, the images of article 12 carried by each path is thereby brought into close proximity on the display tube 32 and may be scanned and defects therein detected substantially simultaneously.

Figure 3:
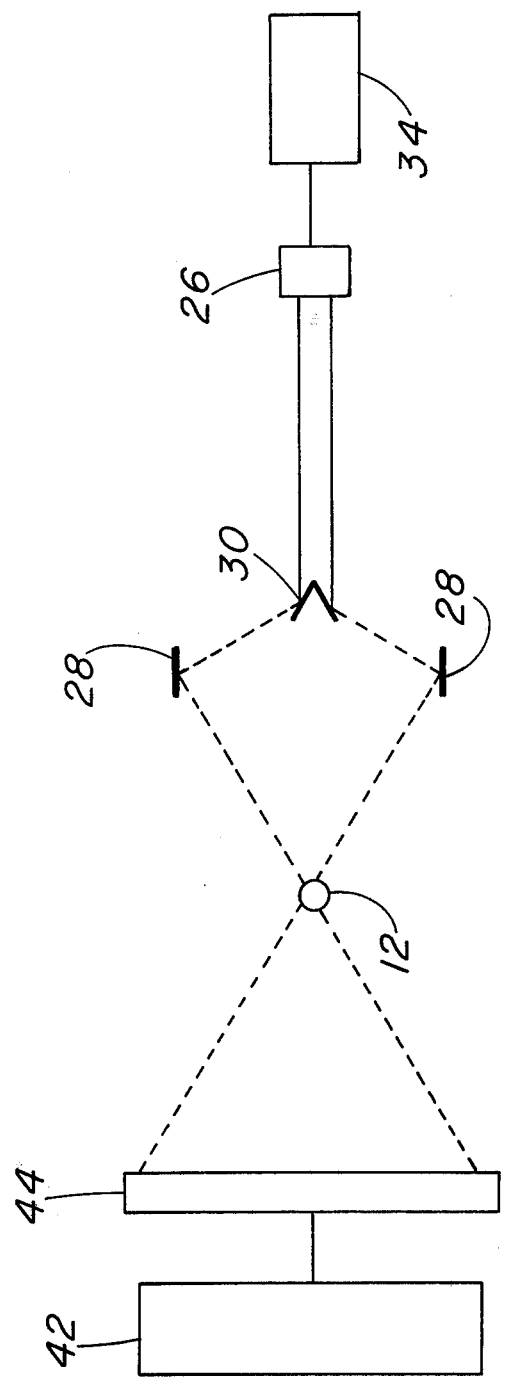
FIG. 3 is a schematic diagram of an alternative embodiment of the present invention.

Referring to FIG. 3, yet another embodiment of the present invention is disclosed. A single radiation source 42 is used in conjunction with beam splitter 44 to produce the decussate paths of light. In this embodiment the reflecting means 28 and 30 are so arranged to cause the paths of light reflected from reflecting means 30 to emerge in a parallel relationship. Camera 26 receives both paths of light and causes the images carried thereby to be displayed and examined in the same fashion as previously explained.

Although a preferred embodiment of the present invention has been illustrated and described, it should be understood that various changes and modifications can be made by those skilled in the art without departing from the spirit and scope of the invention as defined by the following claims.

I claim:
1. An optical system for use in glassware inspection comprising:
   a light source for directing more than one path of light at an article to be inspected;
   first reflecting means;
   second reflecting means and optical receiving means, wherein said first reflecting means and said second reflecting means are positioned to direct said paths of light transferred through said article to said optical receiving means, wherein at least a first path of light and a second path of light impinge simultaneously upon said article at different angles, and wherein said optical receiving means comprises a video camera means for scanning said article and for producing a reject signal when a flaw is present in the article.

2. An optical system for use in glassware inspection as set forth in claim 1 wherein said second reflecting means comprises a first reflecting surface and a second reflecting surface, said first and second reflecting surfaces having an edge juxtaposed and wherein the path of light reflected from said first reflecting surface and the path of light reflected from said second reflecting surface are juxtaposed.

3. An optical system for use in glassware inspection as set forth in claim 1 wherein said light source provides a first path of light and a second path of light, said first and second paths of light simultaneously illuminating only a selected portion of said article, said first and second paths of light forming an acute angle therebetween and wherein said first and second light beams impinge on said article with a path width at least as great as the width of said article.

4. An optical system for use in article inspection comprising:
   a first path of light;
   a second path of light;
   a first reflecting means;
   a second reflecting means; and
   a light sensitive receiving means, wherein said first and second paths of light are decussate paths of light at the area of inspection and simultaneously illuminate the entire width of said article; wherein said second reflecting means comprises a first reflecting surface and a second reflecting surface, said first and second reflecting surfaces having an edge juxtaposed; and wherein said first and second reflecting means are arranged to simultaneously direct the first path of light and the second path of light received through an article being inspected onto said light sensitive receiving means such that two signals are present simultaneously to indicate the presence or absence of any flaws in a single article being inspected.

5. An apparatus for video inspection of articles of manufacture comprising:
   a light source for directing more than one beam of light at a sample article;
   a video camera means for scanning said illuminated sample and for producing for each scan line a video signal corresponding to the difference in refraction characteristics of the portion of the samples scanned;
   means connected to said camera for processing the output signal thereof to produce a defect output signal in response to the scanned defect in said sample;
   light reflecting means for causing said beams of light to be viewed simultaneously by said video camera means, wherein said video camera means simultaneously senses at least two images of said sample article and wherein each said image results from light transmitted through said article at different angles.

6. An apparatus for video inspection of articles of manufactures as set forth in claim 5 wherein said light source provides pulsed illumination and wherein said illumination is substantially collimated.

7. An apparatus for video inspection of articles of manufacture as set forth in claim 6 wherein said sample article is continually moving during inspection.

8. A method for providing a visual display of an object undergoing inspection by directing radiation therethrough comprising the steps of:
    generating two decussate beam-paths of radiation;
    placing the object to be inspected at the point of intersection of saidbeam-paths;
    directing said beam-paths onto a video camera to simultaneously create two displays;
    scanning said displays to sense any imperfections therein; and
    generating a signal when an imperfection is sensed in either display of said object.

9. The method set forth in claim 8 wherein the step of directing said beam-paths onto a radiation sensitive device to simultaneously create two displays includes the step of:
    directing the two beam-paths onto respective beam reflecting surfaces such that the reflected beam-paths are juxtaposed.

10. An apparatus for video inspection of articles of manufacture as set forth in claim 5 wherein the said images are superimposed.

* * * * *